(12) United States Patent
Wang et al.

(10) Patent No.: US 6,664,796 B2
(45) Date of Patent: Dec. 16, 2003

(54) WATER CONTAMINATION SENSING ALGORITHMS FOR ETHANOL CONTAINING FUEL

(75) Inventors: Su-Chee Simon Wang, Troy, MI (US); Yingjie Lin, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/961,699

(22) Filed: Sep. 24, 2001

(65) Prior Publication Data

US 2003/0057969 A1 Mar. 27, 2003

(51) Int. Cl.$^7$ ............................ G01R 27/26; B60Q 1/00
(52) U.S. Cl. .................... 324/694; 324/664; 340/450.2
(58) Field of Search ..................... 73/61.43; 702/22–25, 702/30–32, 47, 50, 52, 53, 55, 114, 183, FOR 115–121, FOR 127, FOR 128, FOR 134, FOR 120; 324/694, 691, 664; 340/438, 450

(56) References Cited

U.S. PATENT DOCUMENTS

| 4,474,051 A | * | 10/1984 | Fukuda et al. | ............. | 73/19.01 |
| 5,179,926 A | * | 1/1993 | Ament | ........................ | 123/494 |
| 5,216,409 A | * | 6/1993 | Ament et al. | ................ | 340/438 |
| 5,911,872 A | * | 6/1999 | Lewis et al. | ................. | 205/787 |

* cited by examiner

Primary Examiner—N. Le
Assistant Examiner—Vincent Q. Nguyen
(74) Attorney, Agent, or Firm—Margaret A. Dobrowitsky

(57) ABSTRACT

A method for determining a level of water contamination in a fuel containing ethanol, including determining the ethanol concentration of the fuel; sensing the resistance of the fuel; determining a resistance limit of the fuel; and comparing the resistance to the resistance limit to provide the level of water contamination. Ethanol concentration is preferably obtained by comparing a measured capacitance to known values in a look-up table. The resistance limit can be determined by multiplying a resistance corresponding to the ethanol concentration by an alarm fraction. The resistance is obtained by a look-up table of resistance values at known water contamination levels. Reporting occurs when the measured resistance is at or below the resistance limit. Alternatively, the measured resistance is normalized with respect to the resistance with no water contamination and reporting occurs when −1.6667*normalized resistance+1.6667 approaches 1.0.

20 Claims, 3 Drawing Sheets

WATER CONTAMINATION SENSING ALGORITHMS FOR ETHANOL CONTAINING FUEL

TECHNICAL FIELD

The invention relates in general to sensing algorithms in automotive fuel blends.

BACKGROUND OF THE INVENTION

Ethanol is a common replacement for gasoline in automotive fuel blends. However, fuel containing ethanol tends to absorb moisture from the atmosphere. Too much water condensed in the fuel causes phase separation of the gasoline and ethanol with the ethanol and water phase settled at the bottom of the fuel tank of an engine while the gasoline is at the top. If some of the ethanol and water phase is pumped through the fuel system to the engine, the engine may not ignite. Further, water corrodes engine components in time. Thus, water is a contaminant in fuel.

Current fuel sensors are important in the adjustment of the air-to-fuel (A/F) ratio. Adjustment of the A/F ratio is necessary in a vehicle whenever its fuel composition changes, such as a change in the ethanol content of the fuel. This makes the presence of a real-time on-board fuel sensor to measure the ethanol content in the fuel desirable. While current fuel sensors can be used to estimate the ethanol content, none have the capability of monitoring the water contamination in fuel that can result in phase separation.

SUMMARY OF THE INVENTION

Accordingly, a sensing algorithm, which can be added to current sensors, can monitor the water content in fuel. In doing so, it can signal the driver to prevent phase separation, i.e., the separation of gasoline from ethanol mixed with the water contaminant. Specifically, the present invention is a method for determining a level of water contamination in a fuel containing ethanol, comprising the steps of determining an ethanol concentration of the fuel; sensing a resistance of the fuel; determining a resistance limit of the fuel using the ethanol concentration; and comparing the resistance to the resistance limit to provide the level of water contamination.

In a preferred aspect, the method also comprises the step of measuring a capacitance of the fuel, and the step of determining the ethanol concentration includes the step of comparing the capacitance to values on a look-up table, the look-up table including a plurality of capacitance values and ethanol concentrations corresponding to the plurality of capacitance values.

In one aspect of the invention, the step of determining a resistance limit of the fuel using the ethanol concentration comprises the steps of comparing the ethanol concentration to values on a look-up table, the look-up table including a plurality of ethanol concentrations and resistance values corresponding to the plurality of ethanol concentrations, wherein each resistance value represents a known resistance of fuel at a known level of water contamination; and multiplying a known resistance corresponding to the ethanol concentration by an alarm fraction to obtain the resistance limit. In one variation of this aspect, the known level of water contamination is a level of water contamination just prior to a phase separation. In another variation of this aspect, the known level of water contamination is 0%.

Any of the foregoing aspects can include the step of reporting when the resistance is at or below the resistance limit. Preferably, this step comprises the step of producing an alarm.

In the aspect of the invention wherein the known resistance level corresponding to the ethanol concentration is at a level of water contamination of 0%, a further aspect includes that the alarm fraction is equal to 1.0 and the step of comparing the resistance to the resistance limit to provide the level of water contamination comprises the steps of calculating a normalized resistance by dividing the resistance by the resistance limit; and calculating a water contamination parameter, wherein the water contamination parameter=−1.6667*(normalized resistance)+1.6667. The inventive method according to this aspect can also include the step of reporting when the water contamination parameter is greater than an alarm value, wherein 0<alarm value<1.0.

In yet another aspect of the invention, the step of calculating a resistance limit of the fuel using the ethanol concentration comprises the step of comparing the ethanol concentration to values on a look-up table, the look-up table including a plurality of ethanol concentrations and resistance values corresponding to the plurality of ethanol concentrations, wherein each resistance value represents a known resistance of fuel with no water contamination; and wherein a known resistance corresponding to the ethanol concentration is the resistance limit. In this aspect, the step of comparing the resistance to the resistance limit to provide the level of water contamination can include the steps of calculating a normalized resistance by dividing the resistance by the resistance limit; and calculating a water contamination parameter, wherein the water contamination parameter=−1.6667*(normalized resistance)+1.6667. Preferably, this aspect also includes the step of reporting when the water contamination parameter is greater than an alarm value, wherein 0<alarm value≦1.0.

The step of reporting when the water contamination parameter is greater than an alarm value can comprise the step of producing an alarm.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
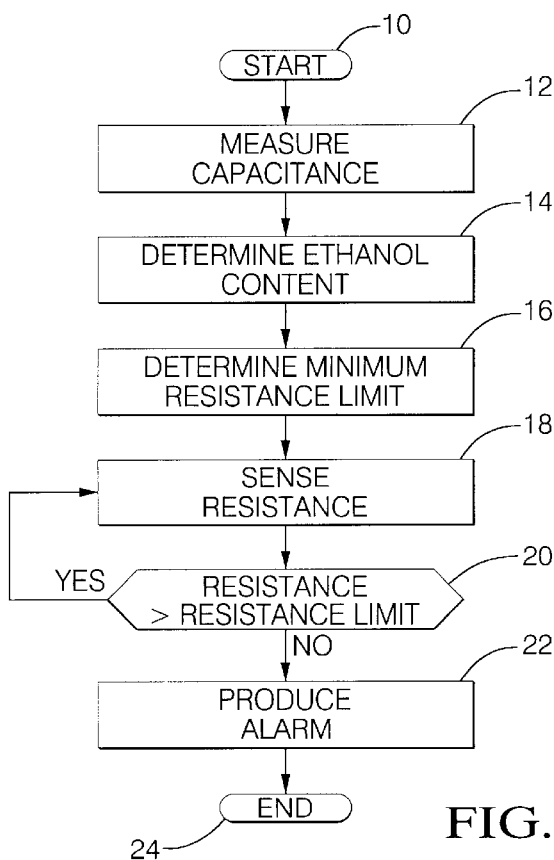
FIG. 1 is a block diagram of one aspect of a sensing algorithm according to the present invention.
Figure 5:
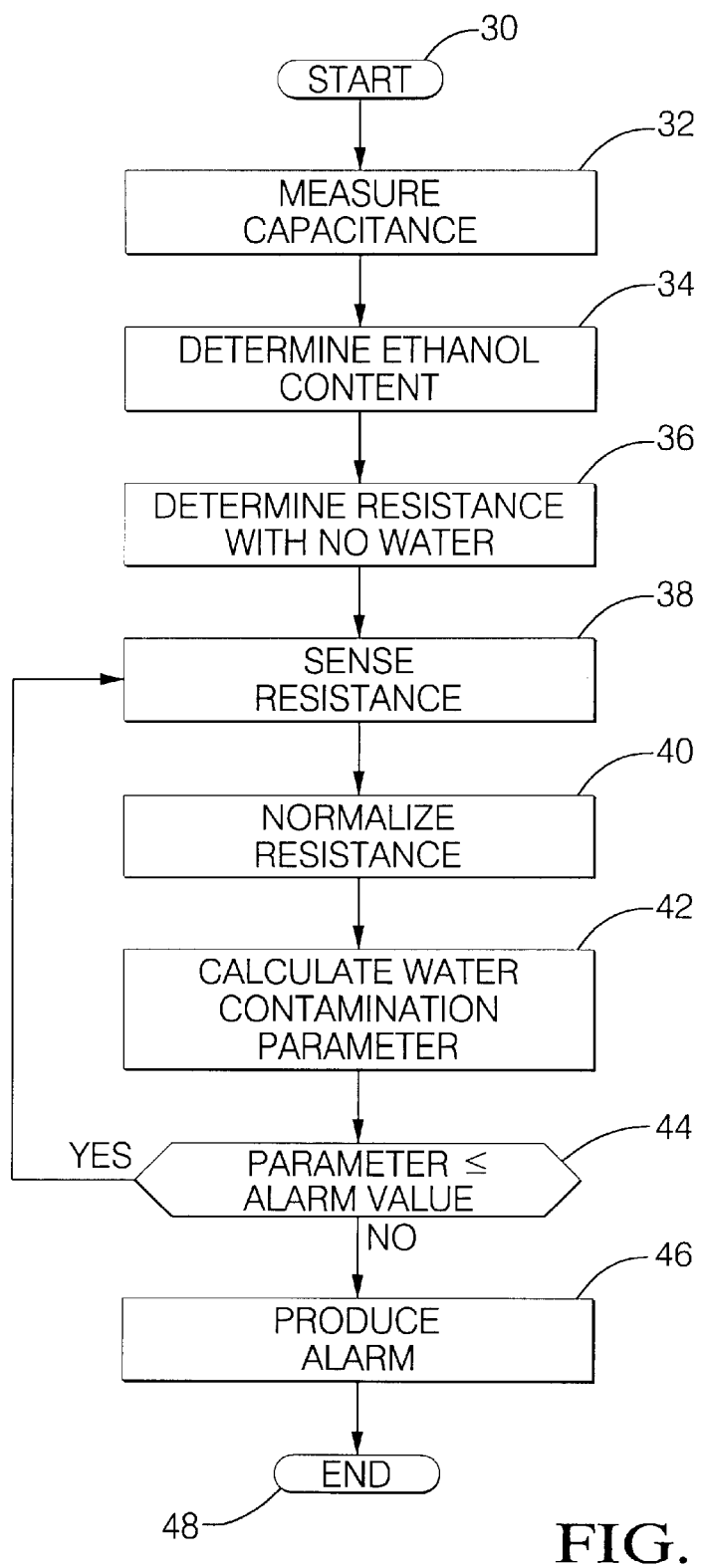
FIG. 5 is a block diagram of a second aspect of the sensing algorithm according to the present invention.

The drawing, particularly FIGS. 1 and 5, show the method of the present invention. Specifically, FIGS. 1 and 5 each show a different aspect of the present inventive method of determining water contamination in fuel. The method incorporates an algorithm stored in preferably a conventional microcontroller of a vehicle, which includes such elements as a central processing unit (CPU), read only memory, random access memory, input/output control circuitry, and analog to digital conversion circuitry. The controller is activated upon application of ignition power to an engine and carries out a series of operations stored in an instructionby-instruction format in memory for providing engine control, diagnostic and maintenance operations.

A first aspect of the invention shown in FIG. 1 starts at step 10 and proceeds to step 12 where capacitance of the fuel is measured. Any type of sensor can be used to determine capacitance. Preferably, the sensor has two interdigitated sensing electrodes coupled to a coaxial cable, the sensor measuring both the capacitance and the resistance of the fuel.

Figure 2:
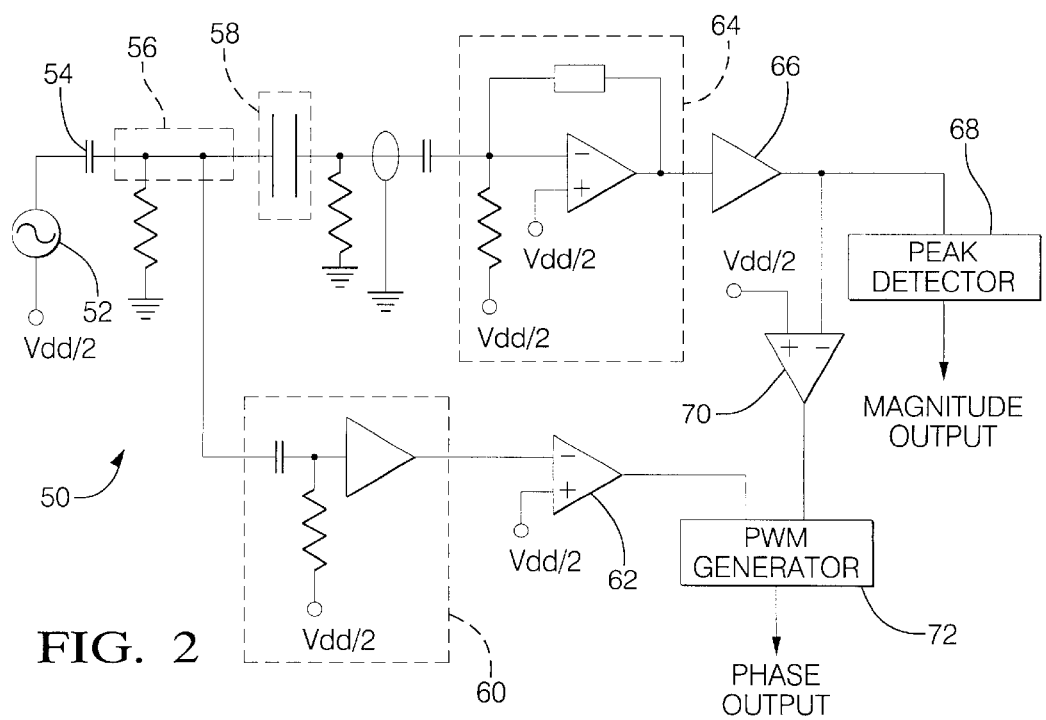
FIG. 2 is one sensor that can be used to measure resistance and capacitance in the present invention.

A block diagram of such a sensor 50 is shown in FIG. 2. The sensing element 58 of a sensor 50 is submerged in the fuel of an engine and excited, then the resistance and capacitance of the fuel are calculated from the induced current measured at the excitation frequency. Specifically, a sinusoidal wave generator 52 supplies a current from 10 kHz to 100 kHz to excite one electrode, or plate, of a sensing element 58. The sinusoidal wave generator 52 generates a wave centered at the voltage Vdd/2, with a peak-to-peak amplitude of around 4 volts. The sinusoidal wave generator 52 is connected to the sensing element 58 at node 56 through a DC block capacitor 54.

Node 56 brings the DC voltage of the excitation plate of the sensing element 58 down to ground through a grounding resistor. At node 56, the circuit of the sensor 50 bifurcates. One path supplies the excitation signal to a DC shift buffer 60. The output from the shift buffer 60 is provided to the inverting input of a comparator functioning as a reference cross detector 62. The non-inverting input is tied to Vdd/2. The output of the reference cross detector 62 is a reference input excitation signal for a pulse width modulated (PWM) generator 72, to be hereinafter discussed.

The other path from node 56 supplies the input stage of the sensor 50 through the sensing element 58. As mentioned, one electrode of the sensing element 58 is connected to the sinusoidal wave generator 52. The other electrode of the sensing element 58 is grounded through a resistor to bring the DC components of the signal to ground. Together with the ground provided for the excitation plate, this ground assures that the signal has no DC components. Also at this electrode, the shield of the shielded cable is grounded. The electrode is then connected through a series capacitor to the inverting input of an amplifier configured as a current-to-voltage converter 64. Feedback is supplied through a feedback impedance, and the inverting input is raised to Vdd/2 through a resistor. The non-inverting input of the comparator is coupled to Vdd/2. The output of the current-to-voltage converter 64 is fed through a conventional amplifier 66.

The output of the amplifier 66, which is the output signal of the input stage, is supplied to two components. First, the output signal is supplied to a peak detector 68 or any kind of an AC amplitude to DC converter that detects the magnitude of the peak of the signal, i.e., a magnitude output. Preferably, the magnitude output is filtered through an active low pass filter (not shown) before being combined with the phase output, to be hereinafter discussed. Second, the output signal of the input stage is supplied to the inverting input of a comparator functioning as a reference cross detector 70. The non-inverting input is tied to Vdd/2. The output of the reference cross detector 70 is the input stage output signal, which is used as an input to the PWM generator 72. As mentioned, the other input to the PWM generator 72 is a reference input excitation signal from the sinusoidal wave generator 52. The output of the PWM generator 72 indicates the phase of the output signal from the input stage, i.e., a phase output. Preferably, the phase output is filtered through an active low pass filter (not shown) before being combined with the magnitude output. Given the magnitude output and the phase output, a controller can determine the resistance and capacitance of the fuel.

Figure 3:
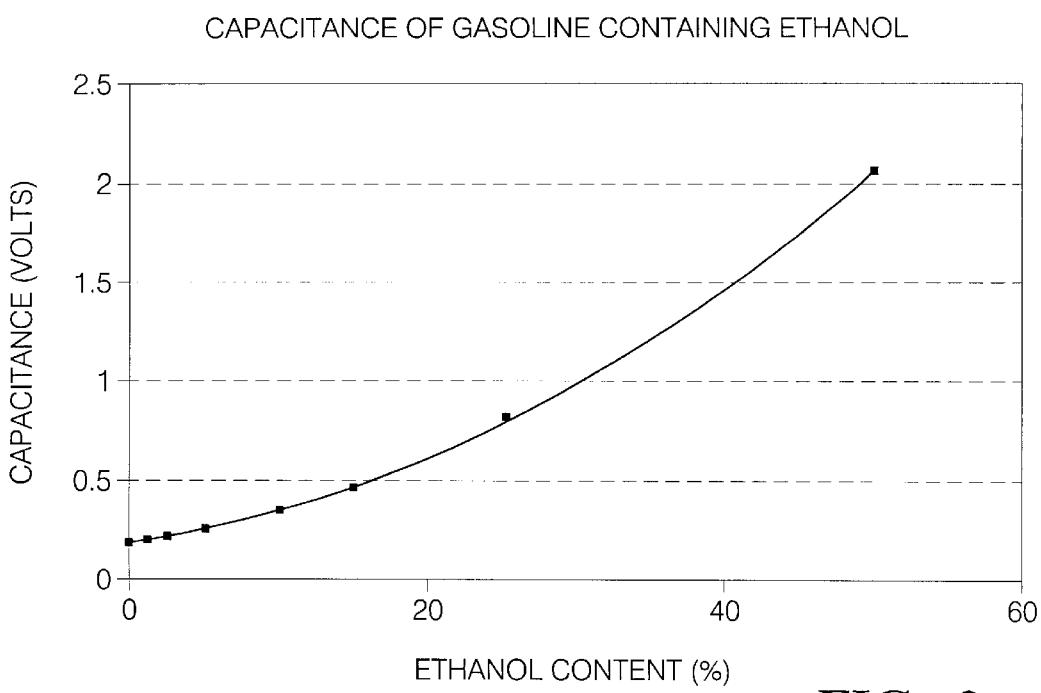
FIG. 3 is a graph showing the capacitance of gasoline related to the ethanol content in the gasoline.

Returning now to FIG. 1, once the capacitance is measured in step 12, the ethanol content of the fuel is calculated from this measured capacitance in step 14. FIG. 3 graphically shows the relationship between ethanol content (in percent) and the measured capacitance of gasoline (in volts) based upon experimental data. In step 14, the measured capacitance can be used in a formula developed from such data, or used with a look up table developed using the data, to obtain ethanol content. Although the invention is described as determining ethanol content based on measuring capacitance, any other means for obtaining ethanol content is also contemplated within the scope of the invention, including the measurement of other parameters indicative of the ethanol content, direct measurement of ethanol content or user input.

Figure 4:
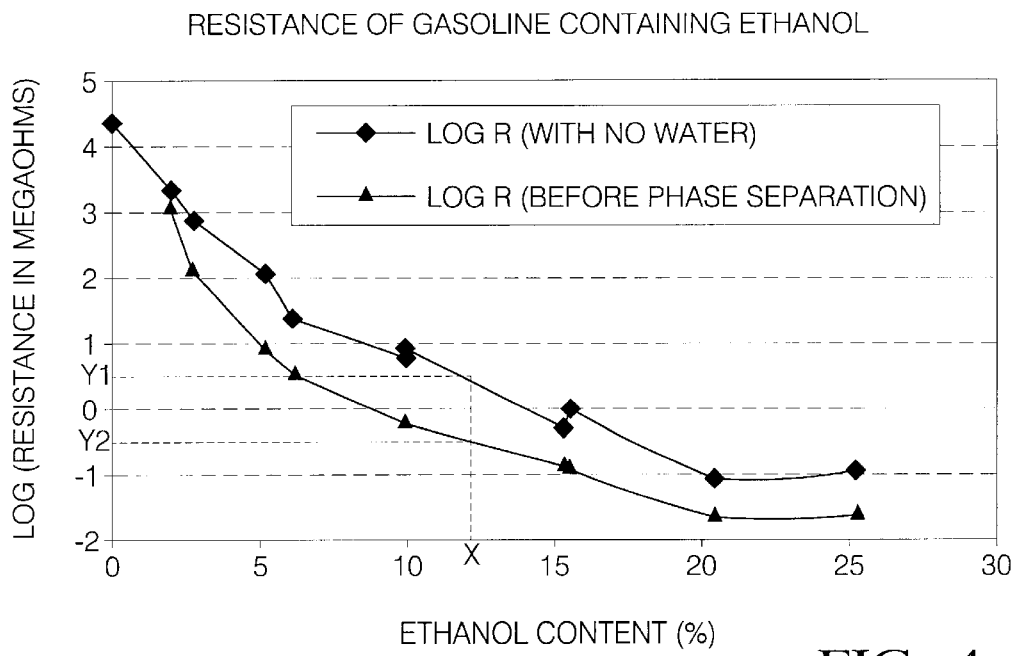
FIG. 4 is a graph showing the resistance of gasoline related to the percentage of ethanol content in the gasoline.

Returning now to FIG. 1, the resistance limit of the fuel containing the percentage ethanol content calculated in step 14 is determined in step 16. The resistance limit represents the highest level of water contamination allowed in the fuel. Preferably, the resistance limit is determined from a look up table developed from data such as that graphically shown in FIG. 4, which was measured experimentally at 20 degrees Celcius. The resistance limit can be calculated from either the high resistance value, i.e., the resistance of the calculated ethanol content with no water, or the low resistance value, i.e., the resistance of the calculated ethanol content when separation occurs due to excessive water contamination. For example, in FIG. 4 the dotted line designated as "X" indicates the ethanol content determined in step 14. The dotted line "Y1" represents the logarithm of the high resistance value, and the dotted line "Y2" represents the logarithm of the low resistance value. The resistance limit, as mentioned, is calculated from either of these values for resistance. Specifically, the resistance limit is calculated by determining either the logarithm of the high or the low resistance value from the look up table, then the logarithmic value is multiplied by an alarm fraction.

The alarm fraction is a fraction representing either how far below the high resistance value the logarithm of the measured resistance can get, or how close to the logarithm of the low resistance value the measured resistance can get, before some corrective action should be taken due to the potential phase separation. For example, if the ethanol content X is 12.3%, and logarithm of the high resistance Y1 is 0.5, the resistance limit can be calculated by multiplying an alarm fraction of −0.9, by example, times 0.5, providing a resistance limit of −0.45, where −0.9 represents how far below the high resistance value the measured resistance can get. Similarly, if the low resistance Y2 of a fuel containing the ethanol content X of 12.3% is −0.5, the resistance limit can be calculated from the logarithm of the low resistance by multiplying an alarm fraction 0.9, for example, times −0.5, providing a resistance limit of −0.45, where 0.9 represents how close the logarithm of the low resistance value the measured resistance can get. Thus, the resistance limit represents a maximum allowed level of water contamination.

Returning now to FIG. 1, the actual resistance of the fuel is measured in step 18, preferably using the same sensor and circuit used in step 12 to measure capacitance. However, any circuit able to measure resistance of the fuel can be used. After the resistance is measured in step 18, the measured resistance is compared to the resistance limit in step 20. Specifically, the logarithm of the measured resistance is compared to see if it is greater than the resistance limit. For example, if the logarithm of the measured resistance is 0.3, this measured value is compared to, using the examples above, −0.45. When the measured value is not above the resistance limit, whichever way the resistance limit is calculated, some type of corrective action can be taken in step 22. For example, an alarm can be produced. The algorithm then ends at step 24. If in step 20, however, the measured value is above the resistance limit, then the resistance is measured again in step 18 and the remainder of the steps are repeated until the engine is off. When the engine starts again, the algorithm starts again at step 10.

FIG. 5 shows another aspect of the present inventive method. Specifically, this aspect starts at step 30 and proceeds to step 32, where the capacitance is measured as discussed in step 12. Then, the ethanol content is calculated in step 34, as discussed with regards to step 14. In step 36, using the ethanol content and the measured capacitance, a resistance is determined based upon the look up table as graphically represented in FIG. 4. In contrast to the aspect of FIG. 1, however, the resistance limit here is the unadjusted logarithm of the high resistance value Y1, that is, where the water content is 0%. In step 38, the resistance of the fuel is measured as described previously with respect to step 18.

In step 40, the logarithm of the measured resistance is normalized with respect to the logarithm of the high resistance value. For example, if the logarithm of the measured resistance is 0.3, and the logarithm of the high resistance value is 0.5, then the normalized resistance is 0.3/0.5=0.6. In step 42, the water contamination parameter is calculated using the normalized resistance determined in step 40 according to the following formula:

$$w.c.p.=-1.6667*(\text{normalized resistance})+1.6667;$$

wherein w.c.p. is the water contamination parameter. Ideally, the normalized resistance is equal to 1.0, and the water contamination parameter is equal to zero. The smaller the normalized resistance, the larger the water contamination parameter. When the water contamination parameter reaches 1.0, which is when the normalized resistance is at about 0.4, separation is likely.

In step 44, the water contamination parameter is compared to an alarm value according to the following formula:

$$\text{alarm value}=1.0 \times \text{contamination percentage};$$

wherein the contamination percentage ranges from 0 to 100 percent of the maximum allowed water contamination. Thus, the alarm value represents the closest the water contamination parameter can get to 1.0, representing likely separation, before corrective action is taken. For example, if the contamination percentage is 0.95, then the water contamination parameter is compared to 0.95 in step 44. If the water contamination parameter is greater than 0.95, then an alarm is produced in step 46, and the algorithm ends at step 48. If, however, the water contamination parameter is less than or equal to 0.95, then the algorithm returns to measure the resistance of the fuel at periodic intervals in step 38 and continues to do so as long as the engine runs, or until the alarm is produced in step 46. After the engine is turned off, the algorithm starts again at step 30 when the engine turns on.

Thus are presented algorithms for sensing the water contamination for ethanol containing fuel. They can be used to monitor the water content in fuel and to prevent phase separation.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for determining a level of water contamination in a fuel containing ethanol, comprising the steps of:

sensing a capacitance of the fuel;

determining an ethanol concentration of the fuel wherein the step of determining the ethanol concentration includes the step of comparing the capacitance to values on a look-up table, the look-up table including a plurality of capacitance values and ethanol concentrations corresponding to the plurality of capacitance values;

sensing a resistance of the fuel;

determining a resistance limit of the fuel using the ethanol concentration; and comparing a logarithm of the resistance to the resistance limit to provide the level of water contamination.

2. The method of claim 1, further comprising the step of:

reporting when the logarithm of the resistance is at or below the resistance limit.

3. The method of claim 2 wherein the step of reporting when the logarithm of the resistance is at or below the resistance limit comprises the step of producing an alarm.

4. The method of claim 1 wherein the step of determining a resistance limit of the fuel using the ethanol concentration comprises the steps of:

comparing the ethanol concentration to values on a look-up table, the look-up table including a plurality of ethanol concentrations and resistance values corresponding to the plurality of ethanol concentrations, wherein each resistance value represents a known resistance of fuel at a known level of water contamination; and multiplying a logarithm of a known resistance corresponding to the ethanol concentration by an alarm fraction to obtain the resistance limit; and wherein the known level of water contamination is a level of water contamination just prior to a phase separation.

5. The method of claim 4 wherein the step of comparing the resistance to the resistance limit to provide the level of water contamination comprises the steps of:

calculating a normalized resistance by dividing the logarithm of the resistance by the resistance limit; and calculating a water contamination parameter, wherein the water contamination parameter=−1.6667*(normalized resistance)+1.6667.

6. The method of claim 5, further comprising the step of:

reporting when the water contamination parameter is greater than an alarm value, wherein 0<alarm value≦1.0.

7. The method of claim 6 wherein the step of reporting when the water contamination parameter is greater than an alarm value comprises the step of producing an alarm.

8. A method for determining a level of water contamination in a fuel containing ethanol, comprising the steps of:

determining an ethanol concentration of the fuel;

sensing a resistance of the fuel;
determining a resistance limit of the fuel using the ethanol concentration; and
comparing the resistance to the resistance limit to provide the level of water contamination; and wherein the step of determining a resistance limit of the fuel using the ethanol concentration comprises the steps of:
  comparing the ethanol concentration to values on a look-up table, the look-up table including a plurality of ethanol concentrations and resistance values corresponding to the plurality of ethanol concentrations, wherein each resistance value represents a known resistance of fuel at a known level of water contamination; and
  multiplying a known resistance corresponding to the ethanol concentration by an alarm fraction to obtain the resistance limit.

9. The method of claim 8, further comprising the step of:
reporting when the resistance is at or below the resistance limit.

10. The method of claim 9 wherein the step of reporting when the resistance is at or below the resistance limit comprises the step of producing an alarm.

11. The method of claim 8 wherein the known level of water contamination is a level of water contamination just prior to a phase separation.

12. The method of claim 11 further comprising the step of:
reporting when the resistance is at or below the resistance limit.

13. The method of claim 12 wherein the step of reporting when the resistance is at or below the resistance limit comprises the step of producing an alarm.

14. The method of claim 8 wherein the known level of water contamination is 0% and wherein the alarm fraction is a single value for any value of ethanol concentration.

15. The method of claim 14, further comprising the step of:
reporting when the resistance is at or below the resistance limit.

16. The method of claim 14 wherein the alarm fraction is equal to 1.0 and wherein the step of comparing the resistance to the resistance limit to provide the level of water contamination comprises the steps of:
  calculating a normalized resistance by dividing the resistance by the resistance limit; and
  calculating a water contamination parameter, wherein the water contamination parameter=−1.6667*(normalized resistance) +1.6667.

17. The method of claim 16, further comprising the step of:
reporting when the water contamination parameter is greater than an alarm value, wherein 0<alarm value<1.0.

18. A method for determining a level of water contamination in a fuel containing ethanol, comprising the steps of:
determining an ethanol concentration of the fuel;
sensing a resistance of the fuel;
determining a resistance limit of the fuel using the ethanol concentration; wherein the step of determining a resistance limit of the fuel using the ethanol concentration comprises the step of comparing the ethanol concentration to values on a look-up table, the look-up table including a plurality of ethanol concentrations and resistance values corresoonding to the plurality of ethanol concentrations, wherein each resistance value represents a known resistance of fuel with no water contamination; and wherein a known resistance corresponding to the ethanol concentration is the resistance limit; and
comparing the resistance to the resistance limit to provide the level of water contamination; wherein the step of comparing the resistance to the resistance limit to provide the level of water contamination comprises the steps of:
  calculating a normalized resistance by dividing the resistance by the resistance limit; and
  calculating a water contamination parameter, wherein the water contamination parameter=−1.6667*(normalized resistance)+1.6667.

19. The method of claim 18, further comprising the step of:
reporting when the water contamination parameter is greater than an alarm value, wherein 0<alarm value≦1.0.

20. The method of claim 19 wherein the step of reporting when the water contamination parameter is greater than an alarm value comprises the step of producing an alarm.

* * * * *